US009039696B2

(12) United States Patent
Assmus et al.

(10) Patent No.: US 9,039,696 B2
(45) Date of Patent: May 26, 2015

(54) HIGH-FREQUENCY SURGICAL DEVICE (75) Inventors: Ilja Assmus, Potsdam (DE); Uwe Fischer, Berlin (DE); Andreas Karrasch, Berlin (DE); Lutz Kersten, Berlin (DE); Stefan Schiddel, Potsdam (DE); Timo Strauss, Gernlinden (DE)

(73) Assignee: OLYMPUS WINTER & IBE GMBH (DE)

( * ) Notice: Subject to any disclaimer, the term of this patent is extended or adjusted under 35 U.S.C. 154(b) by 109 days.

(21) Appl. No.: 13/807,027

(22) PCT Filed: Jun. 24, 2011

(86) PCT No.: PCT/EP2011/060664
§ 371 (c)(1),
(2), (4) Date: Dec. 27, 2012

(87) PCT Pub. No.: WO2012/000912
PCT Pub. Date: Jan. 5, 2012

(65) Prior Publication Data
US 2013/0110103 A1    May 2, 2013

(30) Foreign Application Priority Data

Jun. 28, 2010 (DE) ......................... 10 2010 025 298

(51) Int. Cl.
*A61B 18/18* (2006.01)
*A61B 18/12* (2006.01)
*A61B 18/00* (2006.01)

(52) U.S. Cl.
CPC ............. *A61B 18/1206* (2013.01); *A61B 18/12* (2013.01); *A61B 18/1233* (2013.01); *A61B 2018/0066* (2013.01); *A61B 2018/00928* (2013.01)

(58) Field of Classification Search
USPC .......................................................... 606/38
See application file for complete search history.

(56) References Cited

U.S. PATENT DOCUMENTS 3,801,800 A    4/1974 Newton ................... 307/117
3,897,788 A    8/1975 Newton ................ 128/303.14
(Continued)

FOREIGN PATENT DOCUMENTS

DE    24 29 021    1/1976
DE    101 28 377    1/2003
(Continued)

OTHER PUBLICATIONS

International Search Report and Written Opinion mailed Oct. 12, 2011 in corresponding PCT International Application No. PCT/EP2011/060664.

*Primary Examiner* — George Manuel
(74) *Attorney, Agent, or Firm* — Ostrolenk Faber LLP (57) ABSTRACT The invention relates to a high-frequency surgical device for generating high-frequency energy for cutting and/or coagulating biological tissue. The high-frequency surgical device comprises an application part being electrically connectable to an electrosurgical instrument having at least one activation switch, an intermediary power circuit galvanically separated from the application part, a DC power source which, in operation, provides in the application part at least one DC voltage, a with the DC voltage source electrically connected control signal generator which, in operation, generates in the application part (10) from the DC voltage an alternating control signal with a predetermined switching frequency, and a to the control signal generator electrically connected evaluation unit being electrically connectable to the activation switch of the instrument and which, when the activation switch is actuated, transmits a with the switching frequency oscillating activation signal to the input power circuit.

11 Claims, 6 Drawing Sheets

(56) References Cited

U.S. PATENT DOCUMENTS 5,067,953 A    11/1991  Feucht ............................ 606/34
5,318,563 A *   6/1994  Malis et al. ..................... 606/38

FOREIGN PATENT DOCUMENTS

EP    0 171 967    2/1986
EP    0 186 369    7/1986

* cited by examiner

HIGH-FREQUENCY SURGICAL DEVICE

CROSS-REFERENCE TO RELATED APPLICATIONS

The present application is a 35 U.S.C. §§371 national phase conversion of PCT/EP2011/060664, filed Jun. 24, 2011, which claims priority of German Patent Application No. 10 2010 025 298.0, filed Jun. 28, 2010, the contents of which are incorporated herein by reference. The PCT International Application was published in the English language.

BACKGROUND OF THE INVENTION

The invention relates to a high-frequency surgical device for generating high-frequency energy for cutting and/or coagulating biological tissue, comprising an application part being electrically connectable to an electrosurgical instrument having an activation switch and an intermediary power circuit being galvanically separated from the application part.

High-frequency or HF surgical devices have been known from the prior art for a long time. HF energy generated by a HF surgical device is used e.g. for cutting and coagulating on the human body. For application, an electrosurgical instrument, by which HF energy is introduced into the tissue, is connected to the HF surgical device. In a monopolar application, also a separate neutral or return electrode serving for reverting the energy to the HF surgical device is connected. In a bipolar application, the return electrode is arranged on the instrument.

Modern HF surgical devices, which meet current safety requirements, comprise an application part and an intermediary power circuit galvanically separated therefrom. The electrosurgical instrument with activation switch is connected to the application part. Thus, during electrosurgical application, the application part is in direct contact with a patient's tissue. For reasons of patient's and users safety, the application part and the intermediary circuit are galvanically separated from each other.

To activate the electrosurgical instrument, the activation switch arranged at the instrument is actuated. In instruments which can be used both for coagulating and cutting, two activation switches are provided. One switch activates HF energy suitable for coagulating and the second switch activates HF energy suitable for cutting. The activation switch or the activation switches are electrically connected to the application part. The switching logic of the HF surgical device, which activates the HF energy, is arranged in the intermediary circuit. Thus, the activation signal, i.e. the information on the activation of the instrument, must be transmitted from the application part to the intermediary circuit. Circuitry for evaluating the activation switches are well-known and described e.g. in DE 24 29 021, EP 0 186 369 or also in U.S. Pat. No. 3,801,800.

The system described in DE 101 28 377 operates so that diodes are switched into a circuit in the instrument through activating the activation switch. Via the diodes, a positive or negative half-wave, respectively, of an AC signal, which serves as a control signal, is allowed to pass. Since each activation switch has an associated diode, the actuation of the activation switch is detected from the signal that is being passed through. Alternatively, by connecting the diode, also a portion of the AC signal can be eliminated.

A problem in existing systems is that the HF energy causes interferences which may have negative impact on the AC signal for the activation switches. It may happen that it is not unambiguously determined whether an activation switch is actuated or not, because the difference between control signal and interferences is not detectable. This susceptibility has become particularly apparent at high voltages and currents of the HF signal.

SUMMARY OF THE INVENTION

Thus, it is an object of the present invention to provide an improved HF surgical device in which the actuation of an activation switch of a connected instrument is clearly identified and which is less sensitive to interferences by the HF energy signal.

The object of the present invention is achieved in that the aforementioned HF surgical device comprises a DC voltage source providing a DC voltage in the application part during operation, a control signal generator being electrically connected to the DC voltage source which, during operation, generates from the DC voltage an alternating control signal with a predetermined switching frequency in the application part, and an evaluation unit being electrically connected to the control signal generator and being electrically connectable to the activation switch of the instrument and, when the activation switch is actuated, transmitting a with the switching frequency oscillating activation signal to the input circuit.

The solution according to the present invention has the advantage that a DC voltage is provided in the application part from which the control signal is generated subsequently. From the DC voltage, the control signal can be freely generated. This also permits a low switching frequency which, in absence of the DC voltage source, would not be transferrable to the application part. The low switching frequency differs slightly from the here as interference signal acting high frequency wanted signal. Results have shown that the control signal according to the invention is less susceptible to HF signal interferences.

The invention can be further advanced by preferred embodiments described hereinafter. The features of the embodiments may be combined arbitrarily.

So, the DC voltage source can provide a positive DC voltage and a negative DC voltage in the application part and the evaluation unit can comprise two signal transmitters connected in parallel, wherein one signal transmitter is only activated by a positive voltage, and the other signal transmitter is only activated by a negative voltage. This has the advantage that two activation switches can be detected, one of them via a positive voltage and the other one via a negative voltage. The two signal transmitters, respectively, can be clearly associated to an activation switch, so that for each activation switch a separate activation signal is transmitted into the intermediary circuit. Thus, it is unambiguously determinable which activation switch is actuated and also whether both activation switches are actuated.

In order to achieve particularly fast signal transmission from the application part to the intermediary current circuit, opto-couplers can be used as signal transmitters. Alternatively, e.g. also magneto-couplers can be used.

Further, the evaluation unit can comprise two resistors being connected in parallel, respectively, to a signal transmitter. As a result, a more secure switching behavior of the signal transmitter, in particular of an opto-coupler, is achieved. The resistor reduces a portion of the current signal from the signal transmitter. Thereby, interferences in the voltage signal, which might have led to unintended actuation, can be eliminated.

Additionally or alternatively, the evaluation unit can comprise two Zener diodes which are arranged in series and in reverse direction to the signal transmitter, respectively. As a result, all interferences which are lower than the reverse voltage of the Zener diode are eliminated. The reverse voltage is the voltage above which the current flow is again allowed to pass. This advancement has the advantage that the switching behavior of the signal transmitters becomes substantially digital and, therefore, more reliable.

In order to achieve a preferred digital and, thus, unambiguous switching of the signal transmitters in the evaluation unit, the control signal generator is designed to generate a rectangular signal. In particular, when opto-couplers are used, a rectangular signal is to particularly suitable, because it leads to a digital and, thus, unambiguous switching behavior.

In a particularly preferred embodiment, the control signal generator can comprise an adjustment means, by which the switching frequency of the control signal is variable and adjustable. So, e.g. an additional safety inquiry can be implemented as follows: If the actuation of an activation switch is indicated in the intermediary circuit, the switching frequency in the control signal generator can be modified for short periods of time for confirmation. If this modification in the intermediary circuit is also detected, it is assured that the signal was transferred by the actuation of the activation switch.

Further, the adjustment means can be configured so that information is transferrable in a coded manner through the switching frequency. Thus, the adjustment means can, e.g., transmit operating parameters to the instrument, which are displayed on a display at the instrument. Thus, the operating parameters can be displayed to the user directly at the instrument, where they are clearly visible. In this context, the invention also relates to an electrosurgical system with a high-frequency surgical device according to one of the recited embodiments and to an electrosurgical instrument connected to the high-frequency surgical device, wherein the instrument comprises a read-out unit by which information can be read-out from the control signal.

In order to obtain a control signal being easily distinguishable from the HF signal, the switching frequency of the control signal can be essentially between 100 Hz and 500 Hz. Switching frequencies in this range have proven to be very well identifiable. In HF surgical devices, the HF signal typically has a frequency of approximately 200 kHz to 2 MHz. Thus, 100 Hz to 500 Hz is significantly lower, so that confusions with interferences resulting from the HF current can be excluded.

In a further embodiment, the DC voltage source can provide a voltage of +/−12 V. This is the highest voltage which, according to the current standards, is permissible in the application part and which is also high enough to be clearly distinguished from interferences by the HF signal.

BRIEF DESCRIPTION OF THE DRAWINGS

In the following, the invention is described with reference to the preferred embodiments as shown in the drawings. The individual features can be combined arbitrarily.

First, the invention is described with reference to the embodiments shown in FIGS. 1 to 4.

Figure 1:
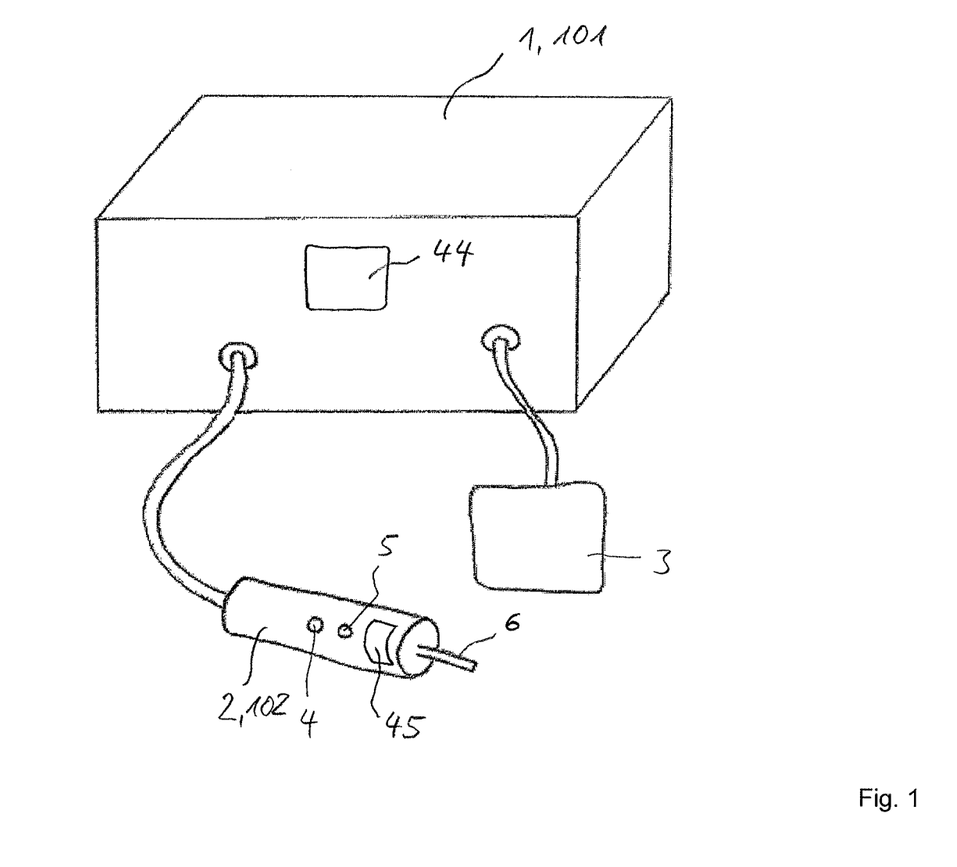
FIG. 1 shows a diagram of an exemplary embodiment of a high-frequency surgical device to according to the invention with a connected instrument.

FIG. 1 shows a HF surgical device 1 to which an electrosurgical instrument 2 and a neutral electrode are connected. The HF surgical device 1 is designed in a manner known per se for cutting and coagulating biological tissue. It comprises a display means 44 for displaying operating parameters, like e.g. operating mode or power. The HF surgical device 1 in FIG. 1 is shown only in very simplified manner. It may feature all typical control elements which, for sake of simplicity, are not shown and not further described herein.

The electrosurgical instrument 2 is designed both for cutting and coagulating biological tissue. It comprises two activation switches 4, 5 and an electrode 6 which, in operation, transfers the HF energy generated by the HF surgical device 1 to the tissue. By means of activation switches 4, 5, the user can activate the HF surgical device 1 in different modes of operation. Switch 4 activates the HF surgical device 1 in the mode cutting, switch 5 in the mode coagulating. Instrument 2, having activation switches 4, 5, can be actuated by a user very easily with one finger. By activating the HF surgical device 1, a high-frequency AC current at electrode 6 is provided, which is a potential risk for user and patient. Therefore, it must be ensured that no erroneous unintentional activation takes place. The actuation of an activation switch 4, 5 has to be unambiguously identified by the HF surgical device 1. Instrument 2 further comprises a display means 45 which, in operation, shows the user the operating parameters on the display means 44 completely or partly.

Identifying the actuation of activation switches 4, 5 according to the invention by the HF surgical device 1 is described hereinafter with reference to FIGS. 2 to 4.

Figure 2:
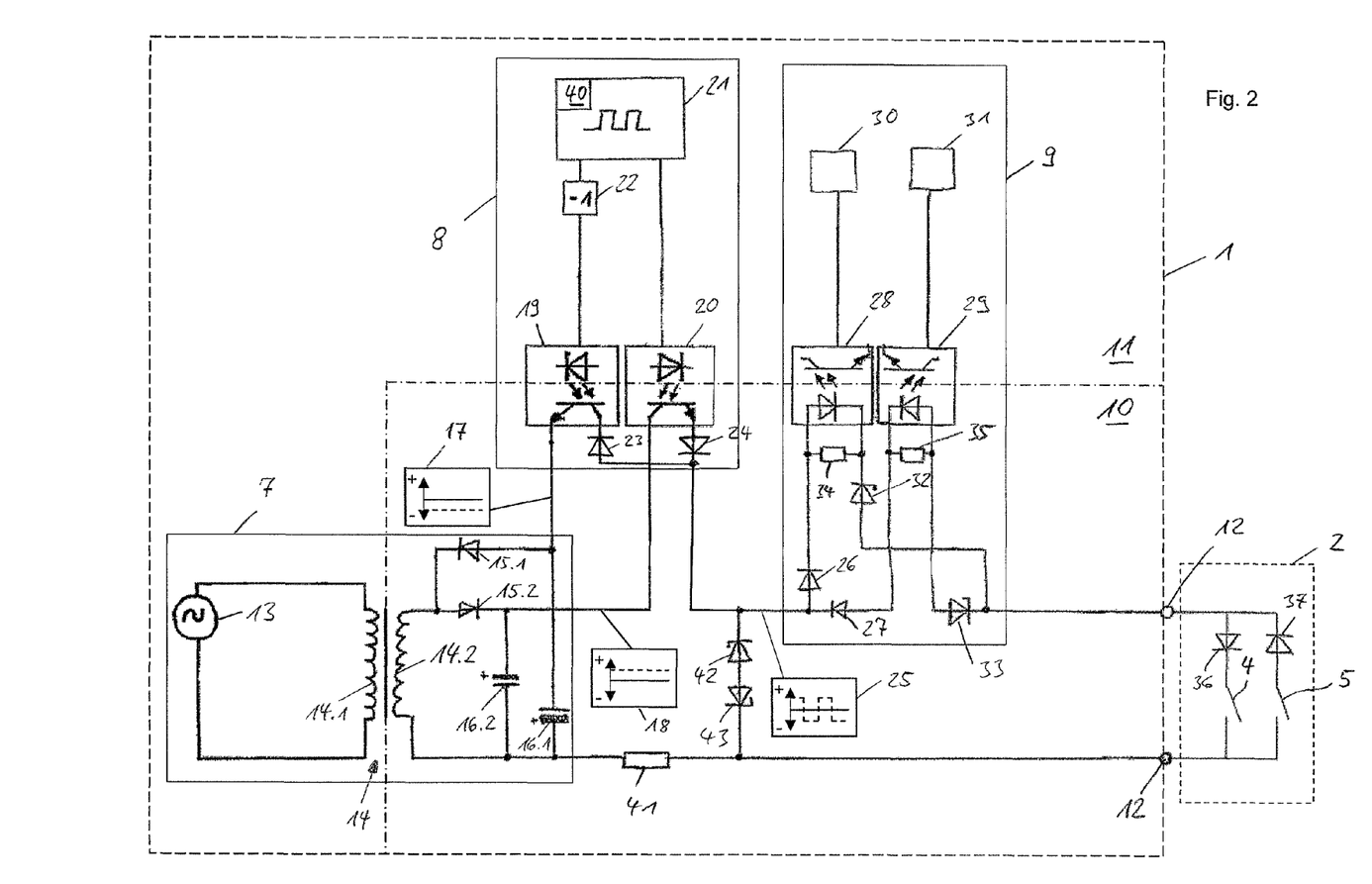
FIGS. 2-4 show diagrams of the exemplary embodiment of FIG. 1 in different switching conditions.

FIG. 2 shows a schematic diagram of the HF surgical device 1 and of the connected instrument 2. The electrical connection is provided by two connection contacts 12 of the HF surgical device 1. For sake of simplicity, only parts of the HF surgical device 1 and of the instrument 2, which are relevant for the identification of activation switches 4, 5, are shown. All remaining components of the HF surgical device 1 not being relevant for the identification are not shown in FIG. 2.

DETAILED DESCRIPTION OF THE INVENTION

The illustrated section of the HF surgical device 1 is divided into an application part 10 and a from the application part 10 galvanically separated intermediary circuit 11. During electrosurgical application, the application part 10 is in contact with the patient. Hence, also the connecting contacts 12 for instrument 2 are parts of the application part 10. For sake of security of users and patients, application part 10 and intermediary circuit 11 are galvanically separated. The HF surgical device 1 also has a from the intermediary circuit galvanically separated primary circuit (not shown), in which the supply voltage flows into device 1.

The HF surgical device 1 comprises a DC voltage source 7, a control signal generator 8 and an evaluation unit 9 being electrically connected to each other. As described hereinafter, DC voltage source 7, control signal generator 8 and evaluation unit 9 are designed of individual components, partly being arranged in the application part 10 and partly in the intermediary circuit 11, respectively.

The DC voltage source 7 comprises in the intermediary circuit 11 an AC voltage source 13 and a transformer 14. The AC voltage source 13 provides an AC voltage with a frequency of approximately 100 kHz. Of course, an AC voltage with another frequency can be used, too, e.g. between 50 and 200 kHz. The AC voltage source 13 is connected to the primary side 14.1 of the transformer 14 and forms a circuit so that, during operation, the AC voltage is applied to the primary side 14.1. The AC power source 13 and the primary side 14.1 of the transformer 14 are arranged in the intermediary circuit 11. The AC voltage is transmitted from the primary side 14.1 to the secondary side 14.2 being arranged in the application part 10. The transformer 14 is designed in this embodiment such that an AC voltage with approximately +/−14 V is fed into the application part 10. The secondary side 14.2 of the transformer 14 is connected to two diodes 15 connected in parallel and to two capacitors 16 connected in parallel. The diodes are arranged such that their reverse direction is oppositely directed.

During operation, the AC voltage source 13 generates an AC voltage of 75 kHz, which is fed by the transformer 14 to the application part 10. The AC voltage with 75 kHz is high enough so that it can be transmitted by a relatively small transformer 14, which has a positive effect on the size of the HF surgical device 1. Lower frequencies require a larger transformer. The AC voltage of +/−14 V transmitted to the application part 10 is rectified by the diodes 15. Diode 15.1 only allows negative half-waves to pass, diode 15.2 only allows positive half-waves to pass, so that a negative and a positive voltage signal are obtained. These voltage signals are smoothed by the capacitors 16, so that AC voltages are formed. Thus, the DC voltage source 7 provides a positive DC voltage 18 and a negative DC voltage 17 in the application part.

The DC voltage source 7 is electrically connected to the control signal generator 8, so that the positive and the negative DC voltage 17, 18 is applied to the control signal generator 8. The control signal generator 8 comprises two opto-couplers 19, 20 as signal transmitters. Of course, also other signal transmitters can be used as opto-couplers. Opto-couplers are particularly suitable, because they transmit the switching signal very quickly. The negative DC voltage 17 is applied to the transistor of the opto-coupler 19, the positive DC voltage 18 to the transistor of the opto-coupler 20. The transistors of the opto-couplers 19, 20 are arranged in the application part 10, the light-emitting diodes of the opto-couplers 19, 20 are arranged in the intermediary circuit 11. In the intermediary circuit 11, the opto-couplers 19, 20 are connected, respectively, to a frequency generator 21, wherein in the opto-coupler 19 an inverter 22 is interposed. The frequency generator 21 has an adjusting means 40 for adjusting the switching frequency. In the application part 10, the opto-couplers 19, 20, respectively, are connected to oppositely arranged diodes 23, 24. Behind the diodes, the signal lines are combined.

The frequency generator 21 generates a rectangular signal with a frequency of approximately 250 Hz, which switches back and forth between a high-signal and a low-signal. The adjustment device 40 also allows for adjusting other frequencies, wherein 250 Hz have proven to be suitable, because the frequency is significantly different to the frequency of the HF signal. The switching frequency can be modified by the adjustment means 40. The adjustment means 40 can also be configured as a variable software parameter. The rectangular signal is transmitted to the opto-couplers 19, 20, whereby the inverter 22 respectively inverts the signal for the opto-coupler 19. Thus, always an inverse signal to the signal being applied to the opto-coupler 20 is applied to the opto-coupler 19. A high-signal allows for switching of opto-couplers 19, 20 so that, in the application part 10, the DC voltages can flow over the transistors of the opto-couplers. Diodes 23, 24 protect the opto-couplers 19, 20. Subsequently, the signals generated by the opto-couplers 19, 20 are being combined. The control signal generator 8 puts out a control signal 25 that alternates between a positive and a negative voltage with a switching frequency of 250 Hz.

The control signal generator 8 is connected to the evaluation unit 9 in the application part 10. The evaluation unit 9 comprises two diodes 26, 27, respectively connected in parallel, two opto-couplers 28, 29 and two Zener diodes 32, 33. Diode 26 only allows positive current to pass, diode 27, having an opposite switching direction, only allows negative current to pass. Diodes 26, 27, respectively, are connected to the opto-coupler 28, 29 as switching means. Diodes 26, 27 and the light-emitting diodes of the opto-couplers 28, 29 are arranged in the application part. In the intermediate circuit 11, the transistors of the opto-couplers 28, 29 and signal output units 30, 31 connected thereto are arranged, respectively, in the intermediary circuit 11. Further, two resistors 34, 35 respectively connected in parallel to the opto-couplers 28, 29, are arranged. The evaluation unit 9 is finally connected to the one connecting contact 12 for the instrument 2.

The control signal 25 is divided in the evaluation unit 9 by the diodes 26, 27. Diode 26 only allows positive currents to pass to the opto-coupler 28, diode 27 only allows negative currents to pass to the opto-coupler 29. Therefore, the opto-coupler 28 switches at each positive impulse of the control signal, so that an activation signal is shown by the signal output unit 30. In the opto-coupler 29, it is accordingly vice versa, such that each negative impulse of the control signal is shown by the signal output unit 31. The signal output units 30, 31 are signal-connected to a control unit (not shown) of the HF surgical device 1 which causes an activation of the HF energy at the electrode 6.

The resistors 34, 35, respectively, serve for eliminating interferences on the signals arriving at the opto-couplers 28, 29 to achieve thereby unambiguous digital switching of the opto-couplers 28, 29. The resistor connected in parallel consumes a portion of the current. This is advantageous, because switching characteristics of opto-couplers are not always digital. Due to interferences, the voltage control signal, in low-condition, can have a level which already allows switching of the opto-coupler 28, 29. Due to the extraction of a portion of the current by the resistor 34, 35, interferences are eliminated or minimized, so that the opto-coupler 28, 29 reliably does not switch in low-condition of the control signal.

The Zener diodes 32, 33 also serve for reducing susceptibility to interference. They are installed such that they block in switching direction of the opto-coupler 28, 29. Current only flows in excess of a predetermined avalanche voltage or cut-off voltage, so that all interferences being below the cut-off voltage are eliminated. In the embodiment of FIG. 2, the cut-off voltage of Zener diodes 32, 33 is approximately 8.2 V. This configuration has proven to be advantageous, because the control signal has +/−12 V and is, therefore, fully allowed to pass. Only interference signals of mostly below 8.2 V are blocked. In the application part, the voltage of +/−12 V is, according to current standards, the maximum permissible voltage. It is high enough to identify the high-condition of the control signal unambiguously.

Instrument 2 being connected to the HF surgical device 1 comprises in the embodiment in FIG. 2, besides the activation switches 4, 5 connected in parallel, two diodes 36, 37 also connected in parallel. The diodes 36, 37 are installed in opposite cut-off directions. In this way, when the activation switch 4 is activated, only positive currents are allowed to pass, when the activation switch 5 is activated, only negative currents are allowed to pass.

The DC voltage source 7, the control signal generator 8, the evaluation unit 9 and the instrument 2 form a circuit which can be closed by the switches 4, 5.

In order that, even during non-activation of the switches 4, 5, a current flows through the DC power source 7, a current path back to the DC power source 7 is provided behind the control signal generator 8. In the current path, two Zener diodes 42, 43 with opposite cut-off direction and a resistor 41 as consumer are arranged. The Zener diodes 42, 43 have a cut-off voltage of approximately 11 V, so that the maximum voltage is limited to approximately 11 V.

By means of the evaluation unit 9 during operation it is evaluated whether an activation switch 4, 5 of the instrument 2 is actuated or not. In FIG. 2, no activation switch 4, 5 is actuated, so that the circuit with DC voltage source 7, control signal generator 8 and evaluation unit 9 is open and no current flows. Consequently, since no control signal 25 arrives at the evaluation unit 9, the signal output units 30, 31 do not output a signal and the electrode 6 of the instrument 2 is not activated.

The actuation of the activation switch 4 and its identification by the HF surgical device 1 according to the invention is described hereinafter with reference to FIG. 3.

Figure 3:
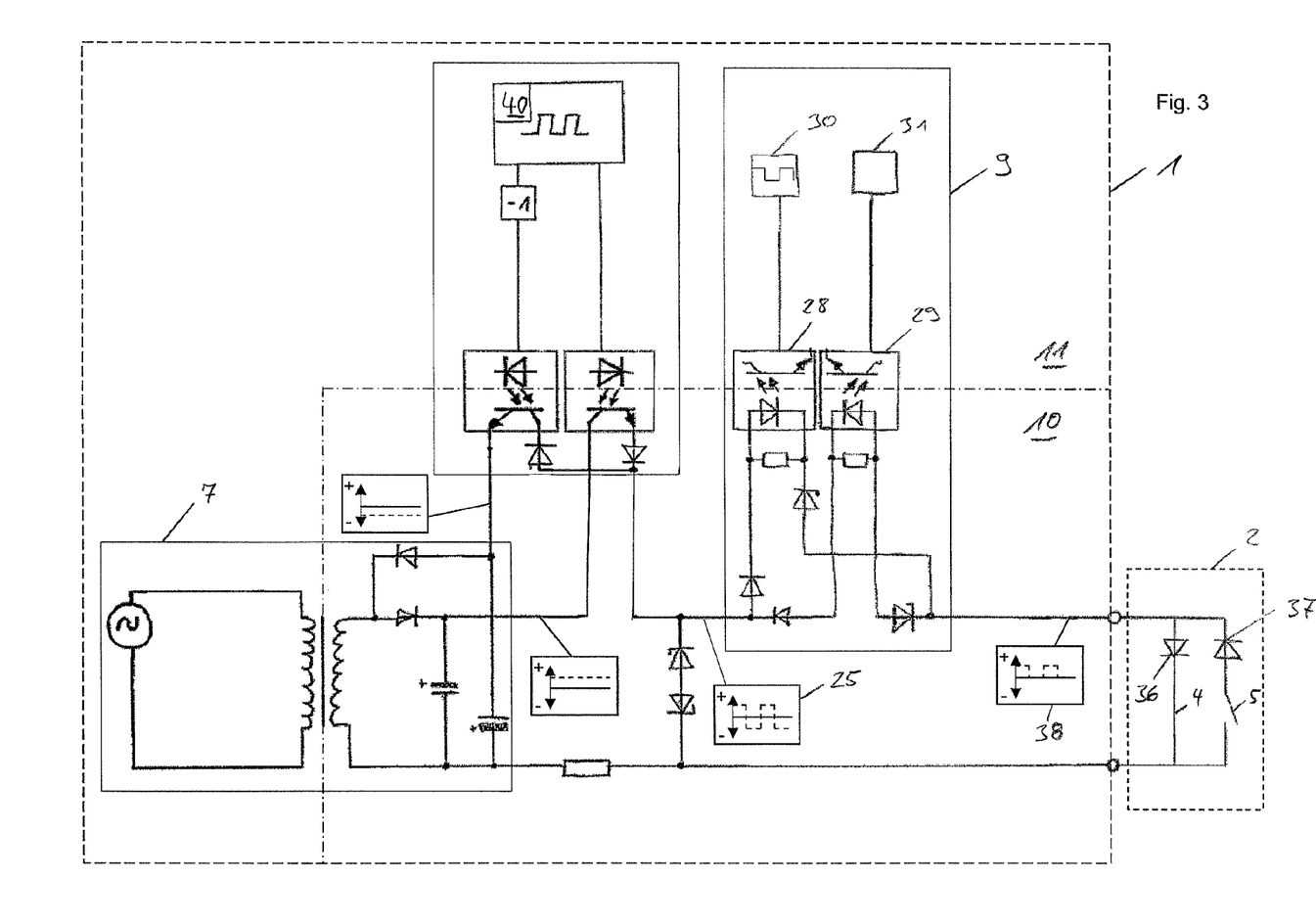

FIG. 3 shows the system comprising the HF surgical device 1 and the instrument 2 of FIG. 2 in operation when the activation switch 4 is actuated and, thus, is closed. When the activation switch 4 is closed, the circuit is closed and the diode 36 allows positive currents to pass. Consequently, the positive portion 38 of the control signal is allowed to pass. This positive control signal 38 with a switching frequency of 250 Hz arrives at the opto-coupler 28 which switches with the switching frequency. The signal output unit 30 outputs an activation signal with the switching frequency and thereby indicates in the intermediary circuit 11 the actuation of the activation switch 4. By means of the activation signal, the HF energy at the electrode 6 suitable for electrosurgical cutting is activated.

For safety testing, the switching frequency of the activation signal can be checked. It must be equal to the frequency of the control signal generator 8. Otherwise, no activation of HF energy takes place.

The actuation of activation switch 5 and its identification by the HF surgical device 1 according to the invention are described hereinafter with reference to FIG. 4.

Figure 4:
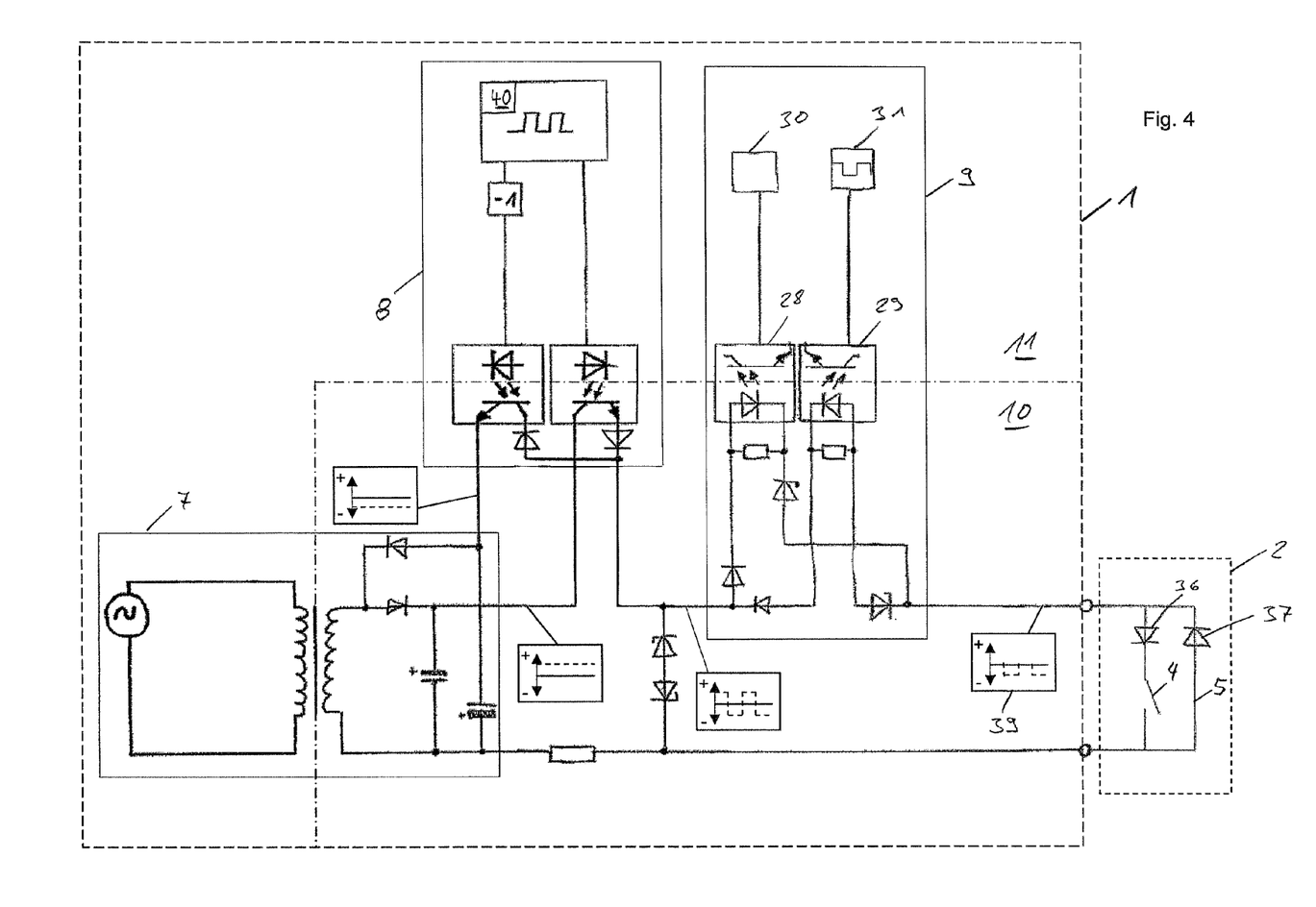

FIG. 4 shows the system comprising the HF surgical device 1 and the instrument 2 of FIG. 2 in operation, when the activation switch 5 is actuated and, thus, is closed. By means of the closed activation switch 5, the circuit is closed and the diode 37 allows negative currents to pass. Consequently, the negative portion 39 of the control signal is allowed to pass. This negative control signal 39 with the switching frequency of 250 Hz arrives at the opto-coupler 29 which switches with the switching frequency. The signal output unit 31 outputs an activation signal with the switching frequency and thereby indicates in the intermediary circuit 11 the actuation of the activation switch 5. Thereby, in the HF surgical device, the HF energy at the electrode 6, being suitable for electrosurgical coagulating, is activated.

When both activation switches 4, 5 are actuated simultaneously, accordingly, positive and also negative portions 36, 39 of the control signal 25 are allowed to pass. Hereby, both opto-couplers 28, 29 switch and both signal output units 30, 31 output signals. Thereby can be unambiguously identified that both activation switches 4, 5 are actuated.

In the following, a further embodiment of the HF surgical device 101 according to the invention is described with reference to FIG. 5. For sake of brevity, only the differences between the embodiments of FIGS. 1 to 4 are referred to. Identical components have identical reference numerals.

Figure 5:
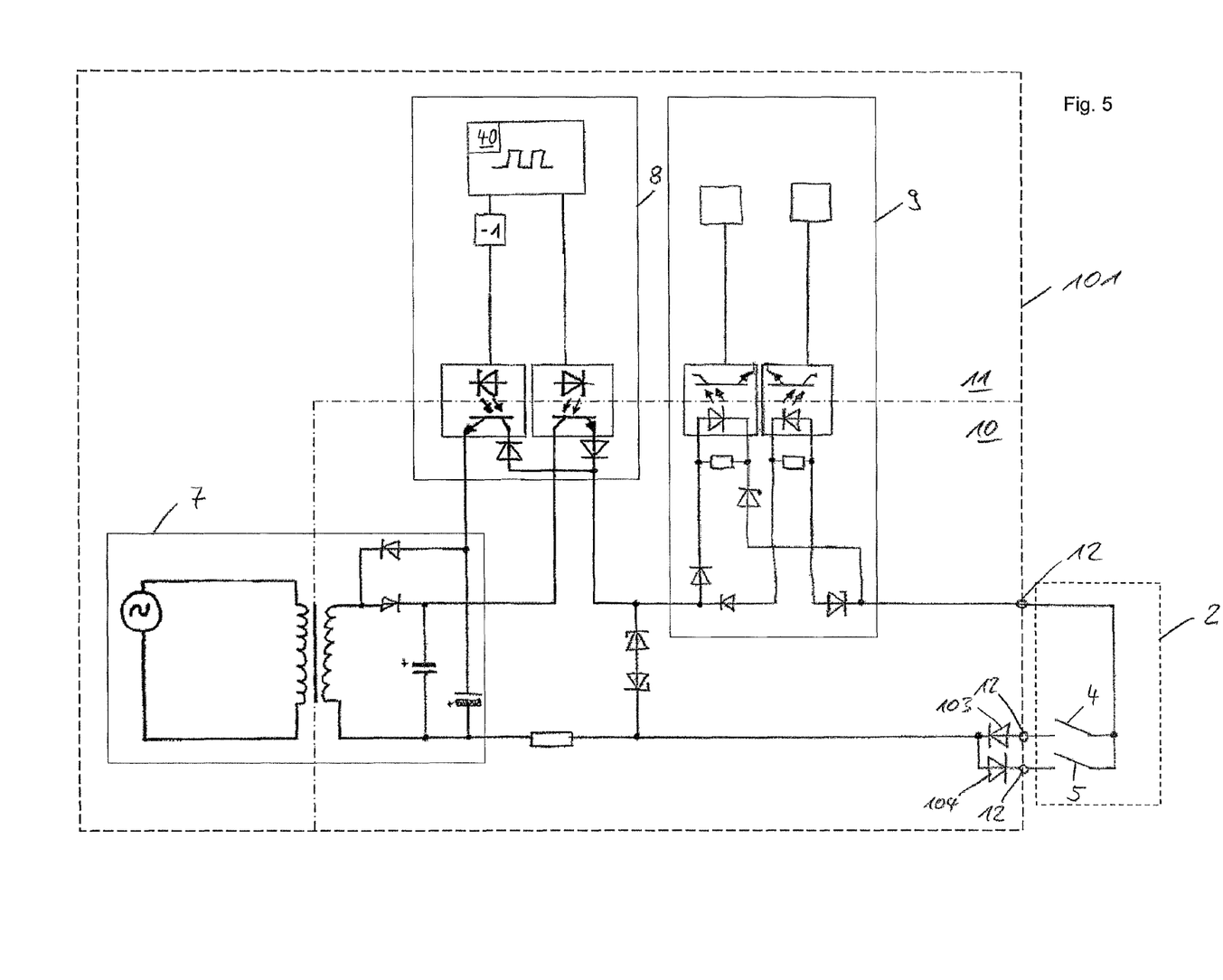
FIG. 5 shows a diagram of a further exemplary embodiment of the high-frequency surgical device with a connected instrument.

To the HF surgical device in FIG. 5, an alternative instrument 102 is connected which does not have diodes 36, 37. Both, instrument 102 and HF surgical device 101, comprise three connection contacts 12. Further, the HF surgical device 101 comprises two diodes 103, 104 connected in parallel. Like diodes 36, 37, also diodes 103, 104 are arranged in series with the activation switches 4, 5. The only difference is that diodes 103, 104 are arranged in the HF surgical device 1 and diodes 36, 37 are arranged in the instrument 2, so that the instrument 2 and the HF surgical device 1 only require two connection contacts 12. The identification of the actuation of activation switches 4, 5 by the HF surgical device 101 is identical to that of HF surgical device 1 as described above with reference to FIGS. 2 to 4.

In the following, a further embodiment of the system according to the invention from the HF surgical device 1 and the instrument 2 is described with reference to FIG. 6. For sake of brevity, only the differences to the embodiment of FIGS. 1 to 4 are referred to. Identical components have identical reference numerals.

Figure 6:
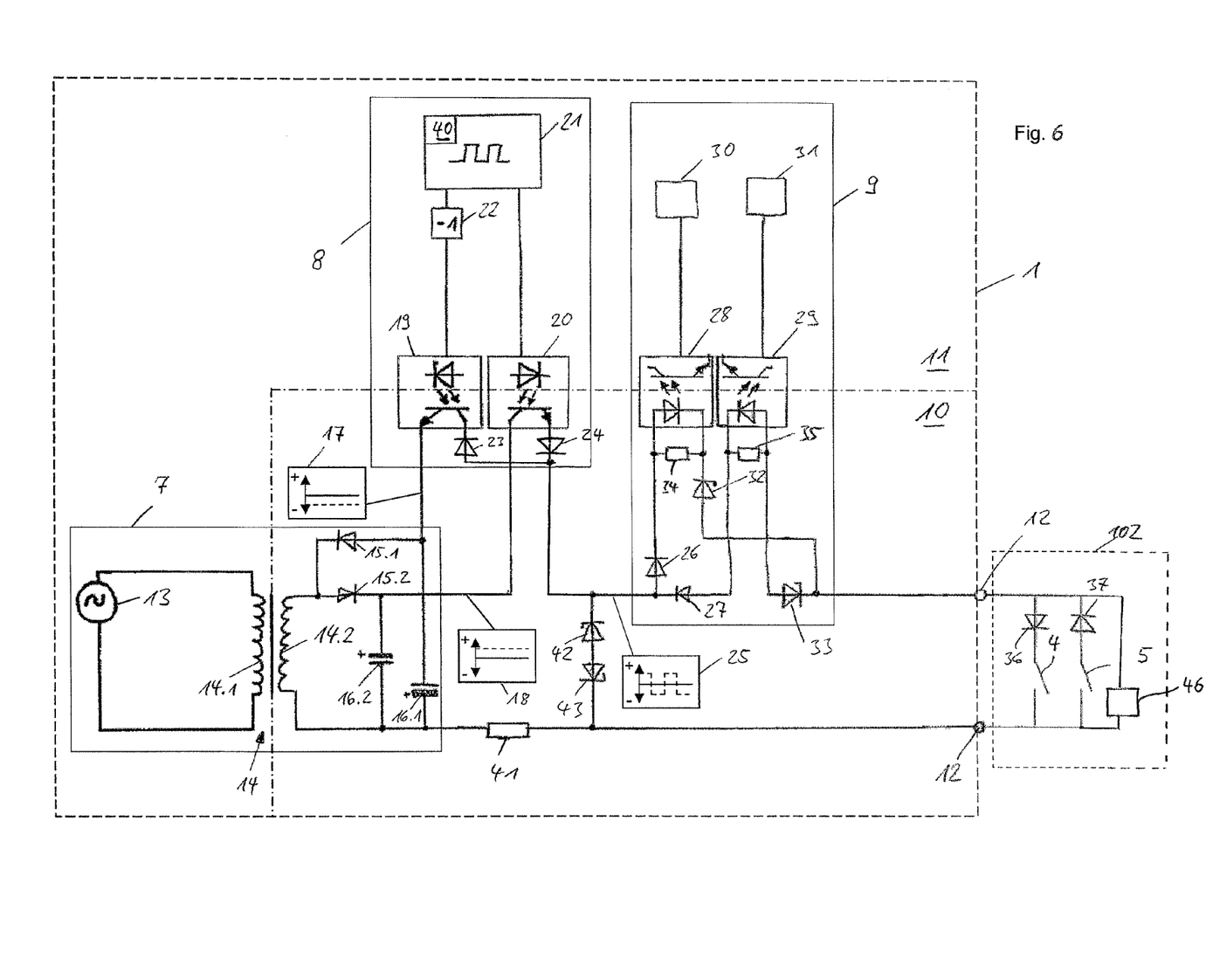
FIG. 6 shows a diagram of a further exemplary embodiment of the high-frequency surgical device according to the invention with a connected instrument.

In FIG. 6, a modified instrument 102 is connected to the HF surgical device 1. The instrument 102 comprises, in addition to the diodes 36, 37 connected in parallel, a read-out unit 46 connected to the connection contacts 12. Information, which is transmitted in encoded form by the control signal 25, can be read-out by the read-out unit 46. This information can e.g. be operating parameters, like power or operating mode, which are shown during operation on the display 45 of instrument 102.

In the HF surgical device according to the invention, information is transmitted in encoded form by the adjustment means 40 by modification of the shifting frequency of the control signal. The information is read-out by the read-out unit 46 without an activation switch 4, 5 being actuated. If an activation switch 4, 5 is actuated and if this is indicated by the signal output units 30, 31, the adjustment means 40 alternates to the predetermined switching frequency of 250 Hz, which then can be verified. During the activation of the instrument, no information transfer takes place. This is also not necessary because, for safety reasons, no alteration of the operating parameters is possible during activation. Further, it is also possible to transmit information in the other direction from the instrument to the HF surgical device 1. For this purpose, the control signal in the instrument is altered and read-out in the HF surgical device.

The invention claimed is:

1. High-frequency surgical device for generating high-frequency energy for cutting and/or coagulating biological tissue, comprising an application part being electrically connectable to a surgical instrument having an activation switch, an intermediary power circuit being galvanically separated from the application part, a DC power source which, in operation, provides a positive and a negative DC voltage in the application part, a control signal generator being electrically connected to the DC voltage source, which generates in the application part, in operation, an alternating control signal with a predetermined switching frequency from the positive and negative DC voltage, and an evaluation unit that is electrically connected with the control signal generator, wherein the evaluation unit is electrically connectable to the activation switch of the instrument and transmits an activation signal that oscillates with the switching frequency into the intermediary power circuit when the activation switch is actuated, and wherein the evaluation unit comprises two signal transmitters being connected in parallel, wherein a first signal transmitter is activated only by a positive voltage and a second signal transmitter is only activated by a negative voltage, and which.

2. High-frequency surgical device according to claim 1, wherein the signal transmitters are opto-couplers.

3. High-frequency surgical device according to claim 1, wherein the evaluation unit comprises two resistors which are connected in parallel, each to a respective signal transmitter.

4. High-frequency surgical device according to claim 1, wherein the evaluation unit includes two Zener diodes which are installed respectively in series and in reverse direction to a signal transmitter.

5. High-frequency surgical device according to claim 1, wherein the control signal generator generates a rectangular signal.

6. High-frequency surgical device according to claim 1, wherein the control signal generator has an adjusting means by which the switching frequency of the control signal is variable and adjustable.

7. High-frequency surgical device according to claim 6, wherein the adjusting means is configured such that information is transferable through switching frequency coding.

8. High-frequency surgical device according to claim 1, wherein the switching frequency of the control signal is substantially between 100 Hz and 500 Hz.

9. Electrosurgical system with a high-frequency surgical device claim 1 and with an electrosurgical instrument being connected to the high-frequency surgical device, wherein the instrument comprises a read-out unit by means of which information is readable from the control signal.

10. High-frequency surgical device, for generating high-frequency energy for cutting and/or coagulating biological tissue, comprising an application part being electrically connectable to a surgical instrument having an activation switch, an intermediary power circuit being galvanically separated from the application part, a DC power source which, in operation, provides a DC voltage in the application part, a control signal generator being electrically connected to the DC voltage source, which generates in the application part, in operation, an alternating control signal with a predetermined switching frequency from the DC voltage, and an evaluation unit that is electrically connected with the control signal generator, wherein the evaluation unit is electrically connectable to the activation switch of the instrument and transmits an activation signal that oscillates with the switching frequency into the intermediary power circuit when the activation switch is actuated, and wherein the evaluation unit comprises two resistors which are connected in parallel each said resistor to a respective signal transmitter.

11. High-frequency surgical device for generating high-frequency energy for cutting and/or coagulating biological tissue, comprising an application part being electrically connectable to a surgical instrument having an activation switch, an intermediary power circuit being galvanically separated from the application part, a DC power source which, in operation, provides a DC voltage in the application part, a control signal generator being electrically connected to the DC voltage source, which generates in the application part, in operation, an alternating control signal with a predetermined switching frequency from the DC voltage, and an evaluation unit that is electrically connected with the control signal generator, wherein the evaluation unit is electrically connectable to the activation switch of the instrument and transmits an activation signal that oscillates with the switching frequency into the intermediary power circuit when the activation switch is actuated, and wherein the signal transmitters are opto-couplers.

* * * * *